(12) United States Patent
Stoneman et al.

(10) Patent No.: US 7,601,676 B2
(45) Date of Patent: Oct. 13, 2009

(54) SULFONATE COMPOSITIONS

(75) Inventors: Kyle D. Stoneman, Fenton, MO (US); Ju-Fu Shiau, Chesterfield, MO (US); Jose Reyes-Gavilan, Glen Allen, VA (US)

(73) Assignee: Afton Chemical Corporation, Richmond, VA (US)

( * ) Notice: Subject to any disclaimer, the term of this patent is extended or adjusted under 35 U.S.C. 154(b) by 478 days.

(21) Appl. No.: 11/174,312

(22) Filed: Jul. 1, 2005

(65) Prior Publication Data

US 2007/0004600 A1    Jan. 4, 2007

(51) Int. Cl.
C07C 303/32 (2006.01)

(52) U.S. Cl. .................................................... 508/390

(58) Field of Classification Search .............. 508/185, 508/186, 232, 371, 390, 391, 403
See application file for complete search history.

(56) References Cited

U.S. PATENT DOCUMENTS

| | | | |
|---|---|---|---|
| 2,237,625 A | 4/1941 | Olin | |
| 2,237,627 A | 4/1941 | Olin | |
| 2,436,046 A | 2/1948 | Lemmon et al. | |
| 2,527,948 A | 10/1950 | Lyon, Jr. et al. | |
| 2,695,316 A | 11/1954 | McBride | |
| 2,995,569 A | 8/1961 | Hamilton et al. | |
| 3,022,351 A | 2/1962 | Mihm et al. | |
| 3,308,166 A | 3/1967 | Biensan et al. | |
| 3,348,611 A | 10/1967 | Reisberg | |
| 3,367,865 A | 2/1968 | Gudelis | |
| 3,392,201 A | 7/1968 | Warner | |
| 3,471,404 A | 10/1969 | Myers | |
| 3,652,410 A | 3/1972 | Hollinghurst et al. | |
| 3,673,090 A | 6/1972 | Walbillig et al. | |
| 3,703,475 A * | 11/1972 | Sias ................. | 516/9 |
| 3,703,504 A | 11/1972 | Horodysky et al. | |
| 3,703,505 A | 11/1972 | Horodysky et al. | |
| 3,796,661 A | 3/1974 | Suratwala et al. | |
| 3,873,454 A | 3/1975 | Horodysky | |
| 4,119,549 A | 10/1978 | Davis | |
| 4,119,550 A | 10/1978 | Davis et al. | |
| 4,140,642 A | 2/1979 | Kistler et al. | |
| 4,147,640 A | 4/1979 | Jayne et al. | |
| 4,191,659 A | 3/1980 | Davis | |
| 4,204,969 A | 5/1980 | O'Brien et al. | |
| 4,218,332 A | 8/1980 | Gast et al. | |
| 4,240,958 A | 12/1980 | Braid | |
| 4,279,762 A | 7/1981 | Lewis et al. | |
| 4,310,471 A | 1/1982 | Oswald et al. | |
| 4,344,854 A | 8/1982 | Davis et al. | |
| 4,414,121 A * | 11/1983 | Aiello ................. | 508/178 |
| 4,472,306 A | 9/1984 | Powers, III et al. | |
| 4,505,830 A | 3/1985 | Vinci | |
| 4,560,488 A | 12/1985 | Vinci | |
| 4,564,709 A | 1/1986 | Koyama et al. | |
| 4,598,026 A | 7/1986 | Vinci | |
| 4,711,736 A | 12/1987 | Horodysky et al. | |
| 4,753,754 A | 6/1988 | Messenger et al. | |
| 4,795,576 A | 1/1989 | Born et al. | |
| 4,954,274 A | 9/1990 | Zaweski et al. | |
| 4,966,720 A | 10/1990 | Degonia et al. | |
| 5,523,005 A | 6/1996 | Di Biase et al. | |
| 5,929,003 A | 7/1999 | De Montlaur | |
| 6,204,226 B1 | 3/2001 | Le Coent et al. | |
| 6,225,267 B1 * | 5/2001 | Eckard et al. ........ | 508/390 |
| 6,410,491 B1 | 6/2002 | Harrison et al. | |
| 2002/0151442 A1 * | 10/2002 | Bardasz et al. ....... | 508/232 |
| 2004/0248996 A1 | 12/2004 | Costello et al. | |

FOREIGN PATENT DOCUMENTS

| | | |
|---|---|---|
| EP | 0312313 A1 | 4/1989 |
| EP | 0765930 A2 | 4/1997 |
| GB | 1162334 | 8/1969 |
| GB | 1308894 | 3/1973 |
| GB | 2232665 | 12/1990 |

* cited by examiner

Primary Examiner—Glenn A Caldarola
Assistant Examiner—Taiwo Oladapo
(74) Attorney, Agent, or Firm—Luedeka, Neely & Graham, PC

(57) ABSTRACT

An alkali metal sulfonate mixture for metalworking applications, a method for making the sulfonate mixture, and compositions containing the sulfonate mixture. The mixture includes a reaction product of a first synthetic mono-hydrocarbyl substituted sulfonic acid having from about 20 to about 50 carbon atoms in the hydrocarbyl substituent, a second synthetic mono-hydrocarbyl substituted sulfonic acid having from about 10 to about 16 carbon atoms in the hydrocarbyl substituent, and an inorganic alkali metal base. The reaction product has a number average molecular weight ranging from about 400 to about 500 and a substantially bimodal molecular weight distribution.

20 Claims, No Drawings

SULFONATE COMPOSITIONS

FIELD OF THE DISCLOSURE

The disclosure relates to lubricant formulations, to alkali metal sulfonate compositions having improved properties, and in particular to a mixture of hydrocarbyl substituted alkali metal sulfonates for metalworking applications and methods for making the mixture of alkali metal sulfonates.

BACKGROUND AND SUMMARY

Hydrocarbyl substituted sulfonates are widely used as emulsifiers for many purposes, including the formulation of emulsifiable lubricating compositions for use in metalworking processes such as metal cutting, grinding, and milling. For many years, natural sulfonates have been used in such applications. Natural sulfonates are relatively inexpensive materials that are by-products of refining processes, however, such natural sulfonates often have wide supply availability fluctuations and have disadvantages with respect to quality and emulsifying properties. In an attempt to improve the emulsifying properties of natural sulfonates, it is customary to associate such natural sulfonates with secondary surface active agents of different types, more especially non-ionic types or fatty acid salts. However, in order to achieve consistent results, the amount of these secondary compounds used differs according to the quality of the natural sulfonate in the composition. Accordingly, there continues to be a need for sulfonates suitable for metalworking applications having improved properties.

With regard to the foregoing, an exemplary embodiment of the disclosure provides an alkali metal sulfonate mixture suitable for metalworking applications. The mixture includes a reaction product of a first synthetic mono-hydrocarbyl substituted sulfonic acid having from about 20 to about 50 carbon atoms in the hydrocarbyl substituent, a second synthetic mono-hydrocarbyl substituted sulfonic acid having from about 10 to about 16 carbon atoms in the hydrocarbyl substituent, and an inorganic alkali metal base. The resulting reaction product has a number average molecular weight ranging from about 400 to about 500 and a substantially bimodal molecular weight distribution.

In another exemplary embodiment, there is provided a method for making an alkali metal sulfonate mixture having improved properties. The method includes the step of charging a mixture of sulfonic acids to a reaction vessel. The mixture of sulfonic acids contains a first synthetic mono-hydrocarbyl substituted sulfonic acid having from about 20 to about 50 carbon atoms in the hydrocarbyl substituent, and a second synthetic mono-hydrocarbyl substituted sulfonic acid having from about 10 to about 16 carbon atoms in the hydrocarbyl substituent. The mixture of sulfonic acids is neutralized with an alkali metal inorganic base selected from the group consisting of sodium hydroxide, potassium hydroxide, lithium hydroxide, sodium carbonate, potassium carbonate, and lithium carbonate to form a reaction product in an oleaginous reaction medium. Water is removed from the reaction product to provide the alkali metal sulfonate mixture having improved properties. The product mixture has a number average molecular weight ranging from about 400 to about 500 and a substantially bimodal molecular weight distribution.

An advantage of exemplary embodiments described herein is that the resulting synthetic sulfonate mixture has superior emulsibility properties and enhanced rust inhibition properties compared to conventional metal sulfonate products typically used for metalworking applications.

DETAILED DESCRIPTION OF EXEMPLARY EMBODIMENTS

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, contain other than carbon in a ring or chain otherwise composed of carbon atoms. Heteroatoms include sulfur, oxygen, nitrogen, and encompass substituents as pyridyl, furyl, thienyl and imidazolyl. In an embodiment of the present invention, no more than two non-hydrocarbon substituent will be present for every ten carbon atoms in the hydrocarbyl group. In another embodiment, no more than one non-hydrocarbon substituent will be present for every ten carbon atoms in the hydrocarbyl group. In yet another embodiment, there will be no non-hydrocarbon substituents in the hydrocarbyl group.

As used herein, the term "percent by weight", unless expressly stated otherwise, means the percentage the recited component represents to the weight of the entire composition.

The term "synthetic sulfonic acids and salts thereof" is used to designate sulfonic acids and salts thereof made by alkylating and sulfonating an aromatic compound and then neutralizing the resulting sulfonic acid. The term "natural sulfonic acids and salts thereof" is used to designate petroleum sulfonic acids and salts thereof made by treating petroleum fractions. In one embodiment of the present invention, the petroleum sulfonic acids and salts thereof made by treating petroleum fractions used may be solvent treated aromatic fractions with sulfuric acid, fuming sulfuric acid, or sulfur trioxide.

Synthetic sulfonate mixtures according to exemplary embodiments of the disclosure include the reaction product of a first synthetic mono-hydrocarbyl substituted sulfonic acid and a second synthetic mono-hydrocarbyl substituted sulfonic acid having a number average molecular weight less than a number average molecular weight of the first synthetic mono-hydrocarbyl substituted sulfonic acid. Accordingly, the first and second mono-hydrocarbyl substituted sulfonic acids may be represented by the following structures:

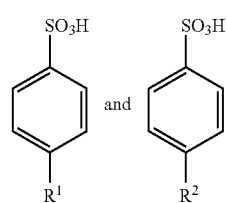

wherein the $R^1$ group is selected from a linear or branched hydrocarbyl group containing from about 20 to about 60 carbon atoms, and the $R^2$ group is selected from a linear or branched hydrocarbyl group containing from about 10 to about 16 carbon atoms. In another embodiment of the present invention, the $R^1$ group may be selected from a dimerized propylene tetramer, a dimerized butylene tetramer, and a mixture thereof wherein the sulfonic acid has a number average molecular weight ranging from about 500 to about 900. In another embodiment of the present invention, the $R^2$ group may be selected from a linear dodecyl group, a branched dodecyl group, and a mixture thereof wherein the sulfonic acid has a number average molecular weight ranging from about 200 to about 380.

Each of the sulfonates in the synthetic sulfonate mixtures according to the disclosure has a molecular weight distribution that complies largely either with Gauss's or with Poisson's law. In particular, the synthetic sulfonate mixtures according to the disclosure exhibit a molecular weight distribution that has two distinct maxima, hereinafter referred to as a "bimodal molecular weight distribution."

In an embodiment of the present invention, the sulfonates are derived from alkylaryl sulfonic acids which have been prepared by sulfonating alkylbenzenes. By alkylbenzenes, it is meant the alkylation products of benzene itself; its homologues with up to about 10 carbon atoms, such as toluene, xylenes, ethylbenzene; the alkylating agent being olefins, olefin oligomers, or chloroparaffins, of appropriate mean molecular weights.

As set forth above, the sulfonate mixtures, according to the disclosure, exhibit a substantially bimodal molecular weight distribution. In general, the first molecular weight distribution maximum ranges from about 300 to about 400 number average molecular weight and the second molecular weight distribution maximum ranges from about 500 to about 900 number average molecular weight. An overall mean number average molecular weight for the mixture ranges from about 400 to about 500. Accordingly, the proportion of first mono-hydrocarbyl substituted sulfonic acid and second mono-hydrocarbyl substituted sulfonic acid in the reaction mixture is selected to provide the desired overall mean molecular weight distribution given the molecular weights of each of the first and second mono-hydrocarbyl substituted sulfonic acids.

Synthetic sulfonate mixtures made from the foregoing sulfonic acids as described herein are salts of the sulfonic acid mixtures wherein the salts may be derived from inorganic or organic bases. In another embodiment of the present invention, the salts of the sulfonic acid mixtures are inorganic salts of sodium. Non-limiting examples of other salts that also be used include but are not limited to ammonium salts, or salts of other alkali metals, or of the alkaline earth metals. The organic bases which may be employed are nitrogen bases, for example, a primary, secondary or tertiary amine, a polyamine, an alkanolamine etc. In an embodiment of the present invention, the organic bases are monoethanolamine, diethanolamine, triethanolamine and mixtures of ethanolamines.

In one embodiment, the sulfonate salt mixture according to the disclosure is prepared via a sodium hydroxide route according to the following reaction:

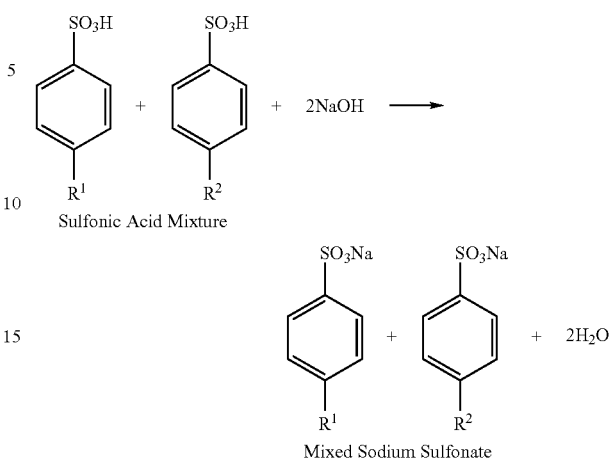

where $R^1$ and $R^2$ are as defined above. In the above reaction, an amount of sodium hydroxide may be used to partially or fully neutralize all of the sulfonic acid present in the reaction mixture.

EXAMPLE 1

In a process for making a sulfonic acid mixture according to the foregoing reaction, a preweighed, baffled reactor equipped with an agitator, temperature controller, and overhead condenser may be used. The reactor is charged with the sulfonic acid mixture indicated in the above reaction in sufficient quantity and ratio to yield a desired target molecular weight of sodium sulfonate mixture. The sulfonic acid mixture includes a dimerized propylene tetramer benzene sulfonic acid or a dimerized butylene tetramer benzene sulfonic acid with a number average molecular weight ranging from about 500 to about 870, and a linear or branched dodecylbenzene sulfonic acid with number average molecular weight ranging from about 316 to about 325.

A neutral oil is charged to the reactor in an amount sufficient to provide a yield of about 50 wt. % to about 60 wt. % activity of final product. Agitation of the sulfonic acid mixture and oil is begun. Next a 50 wt. % sodium hydroxide solution in water is added to the reaction vessel in an amount sufficient to partially or wholly neutralize the sulfonic acid mixture. The rate of addition of sodium hydroxide is controlled to maintain a reaction mass temperature below about 93° C. Once the reaction is complete, the reaction product is slowly heated to about 115° C. over about 1 to about 1½ hours to distill water from the reaction product. The reaction product is then vacuum distilled at about 115° C., under a vacuum of from about 15 to about 30 mm Hg to remove additional water from the reaction product. The product is then cooled to about 80° C. and weighed. A product having from about 50 to about 60 wt. % sulfonate activity and having a mean number average molecular weight ranging from about 400 to about 500 may be made by the foregoing procedure.

In another embodiment, the sulfonate salt mixture according to the disclosure is prepared via a sodium carbonate route according to the following reaction:

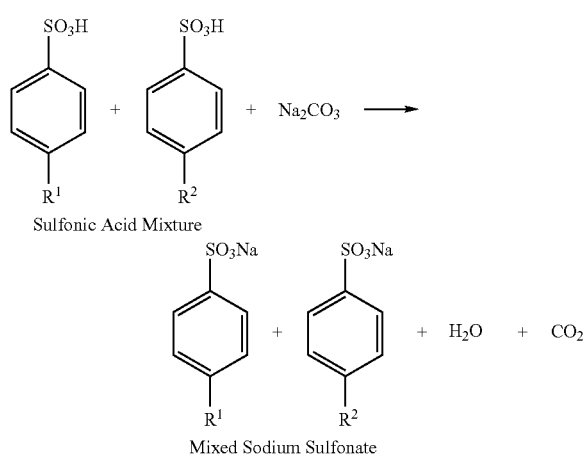

where $R^1$ and $R^2$ are as defined above. In the above reaction, sufficient sodium carbonate may be used to partially or fully neutralize the sulfonic acid mixture.

EXAMPLE 2

In a process for making a sulfonic acid mixture according to the foregoing reaction, a preweighed, baffled reactor equipped with an agitator, temperature controller, and overhead condenser may be used. The reactor is charged with the sulfonic acid mixture indicated in the above reaction in sufficient quantity and ratio to yield a desired target molecular weight of sodium sulfonate mixture. The sulfonic acid mixture includes a dimerized propylene tetramer benzene sulfonic acid or a dimerized butylene tetramer benzene sulfonic acid with a number average molecular weight ranging from about 500 to about 870, and a linear or branched dodecylbenzene sulfonic acid with number average molecular weight ranging from about 316 to about 325.

A neutral oil is charged to the reactor in an amount sufficient to provide a yield of about 50 wt. % to about 60 wt. % activity of final product. Agitation of the sulfonic acid mixture and oil is begun. Next sodium carbonate solid is added to the reaction vessel in an amount sufficient to partially or wholly neutralize the sulfonic acid mixture. The rate of addition of sodium carbonate is controlled to maintain a reaction mass temperature below about 93° C. Once the reaction is complete, the reaction product is slowly heated to about 115° C. over about 1 to about 1½ hours to distill water from the reaction product. The reaction product is then vacuum distilled at about 115° C., under a vacuum of from about 15 to about 30 mmHg to remove additional water from the reaction product. The product is then filtered, cooled to about 80° C. and weighed. A product having from about 50 to about 60 wt. % sulfonate activity and having a mean number average molecular weight ranging from about 400 to about 500 may be made by the foregoing procedure.

Synthetic sulfonate mixtures were prepared according to the foregoing Example 1 and were compared to commercially available products to determine the comparative emulsification performance and rust inhibition characteristics in a metalworking fluid concentrate. The metalworking fluid concentrate samples that were evaluated each contained about 7.5 wt. % of the synthetic sulfonate mixture or about 7.5 wt. % of the commercial product, and 85 wt. % of a 100 SUS naphthenic base oil, from about 1 to about 2 percent by weight alkanol amine, from about 3 to about 4 percent by weight tall oil fatty acid, from about 1 to about 2 percent by weight alkylene glycol, from about 0.5 to about 1.0 percent by weight alkyl phenol ethoxylate, and from about 0.1 to about 1.0 percent by weight potassium hydroxide.

The emulsification test used for comparative purposes was not a standardized test but followed practices typically used by the metalworking fluid industry to assess the stability of a metalworking fluid emulsion. The procedure was as follows:

1) Pour 45 milliliters of water into a 50 milliliter graduated cylinder.
2) Pour 5 milliliters of the metalworking fluid concentrate into the graduated cylinder.
3) Observe bloom performance.
4) Shake the graduated cylinder vigorously with an up-down motion for one to two minutes.
5) Allow the emulsion to stand for 24 hours.
6) Take pictures of emulsion appearance and report volume of cream, oil, and water in the cylinder.

Bloom is defined as the ability of the concentrate to disperse in the water.

Cream is the white creamy layer that sits above the emulsion in the graduated cylinder. It is an indication of the stability of the emulsion. No cream or very low levels of cream indicate a very stable formulation.

Evaluation of the emulsification performance in waters of different hardness is important, since the latter can have deleterious effects on emulsion stability. In the evaluations described above emulsification performance was observed in distilled water, and waters with 300 ppm and 1000 ppm hardness. The procedure outlined in ASTM D 4627 was used to prepare water samples having the desired water hardness.

A standard rust test procedure was used to evaluate the metalworking fluid concentrate samples. The test procedure used was ASTM D 4627—Standard Test Method for Iron Chip Corrosion for Water-Dilutable Metalworking Fluids. The foregoing test procedure is a standardized test set up and published by The American Society for Testing and Materials (ASTM). The procedure is typically used by the industry to evaluate the laboratory rust inhibition performance of metalworking emulsions (i.e., water dilutable fluids). The following is a summary of the test method as set forth in the ASTM D 4627 method:

Cast iron chips are placed in a petrie dish containing a filter paper and diluted metalworking fluid. The dish is covered and allowed to stand overnight. The amount of rust stain on the filter paper is an indication of the corrosion control provided by the fluid.

A range of concentrations of the metalworking fluid concentrates in 100 ppm hard water was used. Concentrations of each of the samples ranged from about 0.5 wt. % to about 10 wt:% of the metalworking fluid concentrate in the 100 ppm hard water. The "breakpoint" concentration is defined as the weakest concentration tested that left no rust stain on the filter paper. The "breakpoint" concentration was used to compare the rust inhibiting properties of each of the samples. In general, the lower the "breakpoint" concentration, the better the performance of the fluid concentrate.

The samples evaluated by the foregoing procedures are identified in the following table as follows:

TABLE 1

| Sample No. | Sodium Sulfonate | Description |
|---|---|---|
| 1 | Synthetic Mixture A | 34 wt. % branched ABSA[1] - MW = 870 (84.4% active) |
| | | 66 wt. % branched ABSA - MW = 325 (95.5% active) |
| | | Ave. MW of NaRSO$_3$[2] = 425. |
| 2 | Synthetic Mixture B | 63 wt. % branched ABSA - MW = 500 (69.5% active) |
| | | 37 wt. % branched ABSA - MW = 325 (95.5% active) |
| | | Ave. MW of NaRSO$_3$ = 425. |
| 3 | Synthetic Mixture B1 | Same as B with a 120% theoretical sodium hydroxide charge to improve flowabilty of product. |
| 4 | Synthetic Mixture C | 66 wt. % branched ABSA - MW = 500 (69.5% active) |
| | | 34 wt. % linear ABSA - MW = 316 (96.5% active) |
| | | Ave. MW of NaRSO$_3$ = 425. |
| 5 | Synthetic Mixture D | 36 wt. % branched ABSA - MW = 500 (69.5% active) |
| | | 66 wt. % linear ABSA - MW = 373 (96.0% active) |
| | | Ave. MW of NaRSO$_3$ = 425. |
| 6 | ALOX 2293 B | Synthetic ABSA. |
| | | Ave. MW of NaRSO$_3$ = 465 |
| 7 | ARISTONATE H | Synthetic ABSA. |
| | | Straight chain mono and dialkylbenzene. |
| | | Avg. MW of NaRSO$_3$ = 520 |
| 8 | ARISTONATE L | Synthetic ABSA. |
| | | Straight chain mono and dialkylbenzene. |
| | | Avg. MW of NaRSO$_3$ = 430 |
| 9 | LOCKSOL 1475 | Natural ABSA. |
| | | Avg. MW of NaRSO$_3$ = 480 |
| 10 | 425-HJ | Synthetic ABSA. |
| | | Avg. MW of NaRSO$_3$ = 400-425 |
| 11 | PETRONATE L | Enhanced (blend of natural with synthetic sodium sulfonates) |
| | | Avg. MW of NaRSO$_3$ = 425 |
| 12 | PETRONATE HL | Enhanced (blend of natural with synthetic sodium sulfonates) |
| | | Avg. MW of NaRSO$_3$ = 455 |
| 13 | PETRONATE HMW | Natural ABSA. |
| | | Avg. MW of NaRSO$_3$ = 550. |
| 14 | QUIRONATE H | Natural ABSA |
| | | Avg. MW of NaRSO$_3$ = 500-550 |
| 15 | QUIRONATE HL | Natural ABSA. |
| | | Avg. MW of NaRSO$_3$ = 440-470 |
| 16 | SYNACTO 416 | Synthetic ABSA. |
| | | Avg. MW of NaRSO$_3$ = 442 |

[1] ABSA = alkylbenzene sulfonic acid
[2] NaRSO$_3$ = Generic formula for sodium sulfonate.

In the foregoing Table 1, sample Nos. 6 and 10 are available from Lubrizol Corporation of Wickliffe, Ohio. Samples 7 and 8 are available from Pilot Chemical Company of Red Bank, N.J. Sample 9 is available from Lockhart Chemical Company of Gibsonia, Pa. Samples 11-13 are available from Crompton Corporation of Middlebury, Conn. Samples 14 and 15 are available from Quidesa of Salamanca, Gto. Mexico. Sample 16 is available from Infineum USA L.P. of Linden, New Jersey.

Results of the emulsion performance test of the metalworking fluid concentrates in Table 1 according to the procedure described above are given in the following Table 2.

TABLE 2

| | Emulsification Performance | | | | | | | | |
|---|---|---|---|---|---|---|---|---|---|
| | Distilled Water | | | 300 ppm Hard Water | | | 1000 ppm Hard Water | | |
| Sample No. | Cream (ml) | Emulsion (ml) | Water (ml) | Cream (ml) | Emulsion (ml) | Water (ml) | Cream (ml) | Emulsion (ml) | Water (ml) |
| 1 | 0-1 | 49-50 | 0 | 0-1 | 49-50 | 0 | 0-1 | 49-50 | 0 |
| 2 | 0 | 50 | 0 | 0 | 50 | 0 | 1 | 49 | 0 |
| 3 | 1 | 49 | 0 | 1 | 49 | 0 | 1 | 49 | 0 |
| 4 | 0-1 | 49-50 | 0 | 1 | 49 | 0 | 1 | 49 | 0 |
| 5 | 0 | 50 | 0 | 0 | 50 | 0 | 1 | 49 | 0 |
| 6 | 1 | 49 | 0 | 1 | 49 | 0 | 1 | 49 | 0 |
| 7 | 1-2 | 48-49 | 0 | 2 | 48 | 0 | 1-2 | 48-49 | 0 |
| 8 | 1 | 49 | 0 | 2 | 48 | 0 | 2 | 48 | 0 |
| 9 | 1 | 49 | 0 | 2 | 48 | 0 | 3 | 47 | 0 |
| 10 | 1 | 49 | 0 | 1 | 49 | 0 | 1-2 | 48-49 | 0 |
| 11 | 0-1 | 49-50 | 0 | 1 | 49 | 0 | 1-2 | 48-49 | 0 |
| 12 | 0 | 50 | 0 | 1 | 49 | 0 | 1 | 49 | 0 |

TABLE 2-continued

| | Emulsification Performance | | | | | | | | |
|---|---|---|---|---|---|---|---|---|---|
| | Distilled Water | | | 300 ppm Hard Water | | | 1000 ppm Hard Water | | |
| Sample No. | Cream (ml) | Emulsion (ml) | Water (ml) | Cream (ml) | Emulsion (ml) | Water (ml) | Cream (ml) | Emulsion (ml) | Water (ml) |
| 13 | 3 | 47 | 0 | 5 | 45 | 0 | 5 | 0 | 45 |
| 14 | 0 | 50 | 0 | 5 | 45 | 0 | 5 | 0 | 45 |
| 15 | 1-2 | 48-49 | 0 | 2-3 | 47-48 | 0 | 3 | 47 | 0 |
| 16 | 1 | 49 | 0 | 2 | 48 | 0 | 2-3 | 47-48 | 0 |

The foregoing results indicate that Sample Nos. 1-5 made according to the disclosure exhibited better emulsification performance than the commercially available sulfonate products of Sample Nos. 6-16.

Results of the corrosion test of the metalworking fluid concentrates in Table 1 according to the procedure described above are given in the following Table 3.

TABLE 3

| | Rust Inhibition Performance |
|---|---|
| Sample No. | Breakpoint Concentration (wt. %) |
| 1 | 5.0 to 7.0 |
| 2 | 4.0 to 5.0 |
| 3 | 4.0 |
| 4 | 4.0 to 7.0 |
| 5 | 7.0 |
| 6 | >10.0 |
| 7 | >10.0 |
| 8 | >10.0 |
| 9 | 10.0 |
| 10 | 10.0 to >10.0 |
| 11 | 10.0 |
| 12 | 10.0 |
| 13 | >10.0 |
| 14 | 10.0 |
| 15 | 10.0 |
| 16 | 7.0 to 10.0 |

The samples in the foregoing Table 3 were emulsified at the concentrations in water with the hardness specified in ASTM D 4627. As shown by the foregoing results, Sample Nos. 1-5 made according to the disclosure exhibited a range of corrosion inhibition performance to a metalworking fluid that is better than the performance of the commercially available products of Sample Nos. 6-15. Only Sample No. 16 comes close to the performance of Sample Nos. 1-5.

Accordingly, emulsifier compositions made in accordance with disclosure give rise to unexpected advantages especially in emulsion stability properties and rust inhibition of metals, which are in many cases superior to the properties and characterstics obtained by use of commercially available sulfonate mixtures now used in the metalworking industry. Furthermore, the sulfonate mixtures according to the disclosure may be prepared to be of substantially constant quality.

The proportions of each sulfonate component in compositions according to the disclosed embodiments are in the range of about 95 to about 5 wt. % of salts of the $R^1$ sulfonic acids and about 5 to about 95 wt. % of salts of $R^2$ sulfonic acids. Other suitable ranges include, but are not limited to (1) about 90 to about 10 wt. % of one of the sulfonic acid salts and about 10 to about 90 wt. % of the other sulfonic acid salt, (2) about 80 to about 20 wt. % of one of the sulfonic acid salts and about 20 to about 80 wt. % of the other sulfonic acid salt.

Normally it will be found that the alkylaryl sulfonate mixtures described above are highly viscous materials and, accordingly, are advantageously diluted either in manufacture, or thereafter, with a suitable diluent/solvent, such as a hydrocarbon oil of the light lubricating oil type. Accordingly, exemplary embodiments within the scope of the disclosure include, but are not limited to, mixtures containing about 50 to about 95 wt. % of the emulsifier composition and about 50 to about 5 wt. % of a solvent/diluent, such as a light lubricating oil, such as a lubricating oil having a viscosity of about 20 to about 40 cSt at about 40° C. However, unless otherwise stated, reference herein to an emulsifier composition is reference only to the sulfonate mixtures and not to any solvent/diluent or components which may be desirable for convenient handling of the sulfonate mixtures.

In accordance with a further feature of the disclosed embodiments, there is provided an emulsifiable mineral oil composition containing a mineral oil and an emulsifier composition containing the sulfonate mixture described herein. Suitable mineral oils are those having a viscosity of from about 5 to about 100 cSt at about 40° C. Of the suitable mineral oils, naphthenic oils may enhance the emulsification of the sulfonate mixture concentrate in water.

Accordingly, the disclosure provides a concentrate for metalworking applications, based on a mineral oil, especially a naphthetic oil, whose viscosity is between about 5 and about 100 cSt at about 40° C., containing from about 5 to about 15% by weight of the alkylaryl sulfonate mixture described herein in addition to one or more surfactants and/or neutralizing agents. Dispersing the foregoing concentrate in water provides a stable aqueous emulsion for metalworking applications. The emulsion is likewise covered by the scope of the disclosure, and may contain from about 80 to about 99% by weight, suitably about 90 to about 98 wt. % water.

Extreme Pressure Agents

Metalworking concentrates of the disclosure may contain at least one sulfur-containing extreme pressure (EP) agent. The sulfur-containing extreme pressure agent may contain at least about 10 percent by weight sulfur. In one embodiment, the amount of said EP agent used in a concentrate is typically sufficient to provide at least about 100 ppm sulfur in the finished metalworking concentrate formulation. In another embodiment, the amount of said EP agent used in a concentrate is typically sufficient to provide at least about 500 to about 30,000 ppm sulfur in the finished metalworking concentrate formulation. In yet another embodiment, the amount of said EP agent used in a concentrate is typically sufficient to provide at least about 650 to about 25,000 ppm sulfur in the finished metalworking concentrate formulation.

A wide variety of sulfur-containing extreme pressure or antiwear agents are available for use in cutting oil compositions provided herein. Among suitable compositions for this use are included sulfurized animal or vegetable fats or oils, sulfurized animal or vegetable fatty acid esters, fully or partially esterified esters of trivalent or pentavalent acids of phosphorus, sulfurized olefins (see for example U.S. Pat. Nos. 2,995,569; 3,673,090; 3,703,504; 3,703,505; 3,796,661; 3,873,454 4,119,549; 4,119,550; 4,147,640; 4,191,659; 4,240,958; 4,344,854; 4,472,306; and 4,711,736), dihydrocarbyl polysulfides (see for example U.S. Pat. Nos. 2,237,625; 2,237,627; 2,527,948; 2,695,316; 3,022,351; 3,308,166; 3,392,201; 4,564,709; and British 1,162,334), functionally-substituted dihydrocarbyl polysulfides (see for example U.S. Pat. No. 4,218,332), and polysulfide olefin products (see for example U.S. Pat. No. 4,795,576).

In an embodiment, a class of extreme pressure agent is made by reacting an olefin, such as isobutene, with sulfur. The product, e.g., sulfurized isobutene (SIB), preferably sulfurized polyisobutylene, typically has a sulfur content of about 10 to about 55%, preferably about 30 to about 50% by weight. A wide variety of other olefins or unsaturated hydrocarbons, e.g., isobutene dimer or trimer, may be used to form the sulfurized olefin extreme pressure agents. Various methods have been disclosed in the prior art for the preparation of sulfurized olefins. See, for example, U.S. Pat. No. 3,471,404 to Myers; U.S. Pat. No. 4,204,969 to Papay et al.; U.S. Pat. No. 4,954,274 to Zaweski et al.; U.S. Pat. No. 4,966,720 to DeGonia et al.; and British Patent No. 1,308,894.

Methods for preparing sulfurized olefins, including the methods disclosed in the aforementioned patents, generally involve multiple stages. The first stage generally involves the formation of a material, typically referred to as an "adduct", in which an olefin is reacted with a sulfur halide, for example, sulfur monochloride. The adduct is then reacted with a sulfur source to provide the sulfurized olefin. The quality of a sulfurized olefin is generally measured by various physical properties, including, for example, viscosity, sulfur content, halogen content and copper corrosion test weight loss (CCT).

U.S. Pat. No. 4,966,720, relates to sulfurized olefins useful as extreme pressure (EP) additives in lubrication oils and to a two stage reaction for their preparation. In the first stage, the reaction temperature between the olefin and sulfur monochloride is maintained from about 0° to about 22° C. in order to make low molecular weight adduct. In the second stage of the reaction a sulfur monochloride/aliphatic monoolefin adduct is reacted in a basic, aqueous alcoholic solution containing sodium sulfide at a temperature of from about 50° C. up to reflux to form the sulfurized olefin.

In another embodiment, a class of such agents is that of polysulfides composed of one or more compounds represented by the formula: $R^6$—$S_x$—$R^7$ where $R^6$ and $R^7$ are hydrocarbyl groups each of which may contain about 3 to about 18 carbon atoms and x may be in the range of from about 2 to about 8. In another embodiment, x may be in the range of from about 2 to about 5. In yet another embodiment, x may be about 3. The hydrocarbyl groups can be of widely varying types such as alkyl, cycloalkyl, alkenyl, aryl, or aralkyl. Tertiary alkyl polysulfides such as di-tert-butyl trisulfide, and mixtures comprising di-tert-butyl trisulfide (e.g., a mixture composed principally or entirely of the tri, tetra-, and pentasulfides) may be used. Examples of other useful dihydrocarbyl polysulfides include the diamyl polysulfides, the dinonyl polysulfides, the didodecyl polysulfides, and the dibenzyl polysulfides.

Anti-Corrosion Agents:

Corrosion inhibitors may also be used in metalworking compositions provided herein. The corrosion inhibitors which may be used include thiazoles, triazoles and thiadiazoles. Examples include benzotriazole, tolyltriazole, octyltriazole, decyltriazole, dodecyltriazole, 2-mercaptobenzothiazole, 2,5-dimercapto-1,3,4-thiadiazole, 2-mercapto-5-hydrocarbylthio-1,3,4-thiadiazoles, 2-mercapto-5-hydrocarbyldithio-1,3,4-thiadiazoles, 2,5-bis(hydrocarbylthio)-1,3,4-thiadiazoles, and 2,5-bis(hydrocarbyldithio)-1,3,4-thiadiazoles. The preferred compounds are the 1,3,4-thiadiazoles, especially the 2-hydrocarbyldithio-5-mercapto-1,3,4-dithiadiazoles and the 2,5-bis(hydrocarbyldithio)-1,3,4-thiadiazoles, a number of which are available as articles of commerce.

Other suitable inhibitors of corrosion include ether amines; polyethoxylated compounds such as ethoxylated amines, ethoxylated phenols, and ethoxylated alcohols; imidazolines; and the like. See, for example, U.S. Pat. Nos. 3,663,561 and 4,097,387. Concentrations of up to about 3 wt. % in a concentrate containing the sulfonate mixture are typical. Preferred corrosion inhibitors include ashless dialkyl thiadiazoles. Such ashless dialkyl thiadiazoles are available from Afton Chemical Corporation of Richmond, Va.

Dialkyl thiadiazoles which may be used are of the general formula:

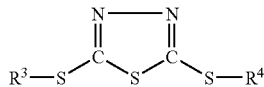

wherein $R^3$ is a hydrocarbyl substituent having from about 6 to about 18 carbon atoms; $R^4$ is a hydrocarbyl substituent having from about 6 to about 18 carbon atoms; and may be the same as or different from $R^3$. In another embodiment, $R^3$ and $R^4$ have about 9-12 carbon atoms. In yet another embodiment, $R^3$ and $R^4$ each have about 9 carbon atoms.

Mixtures of dialkyl thiadiazoles of above formula with monoalkyl thiadiazoles may also be used within the scope of the exemplary embodiments. Such mono alkyl thiadiazoles occur when either substituent $R^3$ or $R^4$ is H.

Rust Inhibitors

Rust inhibitors may optionally be included in cutting oil formulations as described herein. Rust inhibitors may be a single compound or a mixture of compounds having the property of inhibiting corrosion of ferrous metal surfaces. Such materials include oil-soluble monocarboxylic acids such as 2-ethylhexanoic acid, lauric acid, myristic acid, palmitic acid, oleic acid, linoleic acid, linolenic acid, behenic acid, cerotic acid, etc., and oil-soluble polycarboxylic acids including dimer and trimer acids, such as are produced from tall oil fatty acids, oleic acid, linoleic acid, or the like.

Other suitable corrosion inhibitors include alkenylsuccinic acids in which the alkenyl group contains about 10 or more carbon atoms such as, for example, tetrapropenylsuccinic acid, tetradecenylsuccinic acid, hexadecenylsuccinic acid, and the like; long-chain alpha,omega-dicarboxylic acids in the molecular weight range of about 600 to about 3000; and other similar materials.

Rust inhibitors as described above are commercially available from various commercial sources, such as, for example, dimer and trimer acids sold by Crompton Corporation of Middlebury, Conn. under the trade name HYSTRENE and sold by Cognis Corporation of Cincinnati, Ohio under the trade name EMPOL.

Another useful type of acidic corrosion inhibitors are the half esters of alkenyl succinic acids having about 8 to about 24 carbon atoms in the alkenyl group with alcohols such as the polyglycols. Especially preferred rust inhibitors include the primary and secondary amine compounds taught herein as the amine portion of the salt of a phosphoric acid ester as well as mixtures of said amines with other rust inhibitors described above.

Anti-Bacterial Agents:

Bactericides and biocides such as dehydroacetic acid, cresol, ethylene diamine and the like may be used. Other biocides include the 3-isothiazolones as described in U.S. Pat. No. 4,279,762, for example, isothiazolin-3-ones including 2-n-octyl-4-isothiazolin-3-one (commercially available from Rohm and Haas under the trademark Kathon 893 MW) and a mixture of 5-chloro-2-methyl-4-isothiazolin-3-one and 2-methyl-4-isothiazolin-3-one (commercially available from Rohm and Haas under the trademark Kathon MWC). Other commonly used biocides include sodium pyridine-2-thiol-1-oxide (commercially available under the trademark Sodium Omadine from Arch Chemicals) and 3-iodo-2-propynyl-N-n-butyl carbamate (commercially available under the trademark Troysan polyphase from Troy Corporation).

Dispersants

Dispersants which may be included in metalworking concentrates as described herein, include, but are not limited to, an oil soluble polymeric hydrocarbon backbone having functional groups that are capable of associating with particles to be dispersed. The polymeric hydrocarbon backbone may have a weight average molecular weight ranging from about 750 to about 1500 Daltons. Typically, the dispersants comprise amine, alcohol, amide, or ester polar moieties attached to the polymer backbone often via a bridging group. Dispersants may be selected from Mannich dispersants as described in U.S. Pat. Nos. 3,697,574 and 3,736,357; ashless succcinimide dispersants as described in U.S. Pat. Nos. 4,234,435 and 4,636,322; amine dispersants as described in U.S. Pat. Nos. 3,219,666, 3,565,804, and 5,633,326; Koch dispersants as described in U.S. Pat. Nos. 5,936,041, 5,643,859, and 5,627,259, and polyalkylene succinimide dispersants as described in U.S. Pat. Nos. 5,851,965; 5,853,434; and 5,792,729.

Other Ingredients

Alkanol amines may also be included in the metalworking concentrates described herein. Such alkanol amines typically contain from about one to about three aliphatic radicals, each containing from about one to about four carbon atoms, and have at least one hydroxy group attached to a carbon atom, and include primary, secondary and tertiary alkylol amines such as mono-di- or triethanolamine. Use of an excess of alkanol amine relative to the total acid content of the concentrate is desirable.

A coupling agent such as a non-ionic wetting agent may also be used for aqueous metalworking fluid concentrates as provided herein. To improve the compatibility of the components of the concentrate, any desired non-ionic wetting agent may be used, such as a condensation product of ethylene oxide, a condensation product of a fatty acid or derivative, such as a derivative of a fatty acid, fatty alcohols, fatty amide or fatty amine, with ethylene oxides and a reaction product obtained by the condensation of an oxyalkylaryl compound, such as a derivative of an alkylphenol or alkylnaphthol, with ethylene oxide. In an embodiment, the non-ionic wetting agent used may be water-soluble. Typical non-ionic wetting agents include the polyethoxyesters of fatty acids, the monooleate of a polyethylene glycol, the monolaurate of a polyethylene glycol, the polyethoxyethers of fatty alcohols, the condensation product of an alkylphenol such as dodecyl phenol with about 12 moles of ethylene oxide, and the sulfonated product of the condensation of an alkylphenol or an alkylnaphthyl with ethylene oxide.

At numerous places throughout this specification, reference has been made to a number of U.S. Patents. All such cited documents are expressly incorporated in full into this disclosure as if fully set forth herein.

The foregoing embodiments are susceptible to considerable variation in its practice. Accordingly, the embodiments are not intended to be limited to the specific exemplifications set forth hereinabove. Rather, the foregoing embodiments are within the spirit and scope of the appended claims, including the equivalents thereof available as a matter of law.

The patentees do not intend to dedicate any disclosed embodiments to the public, and to the extent any disclosed modifications or alterations may not literally fall within the scope of the claims, they are considered to be part hereof under the doctrine of equivalents.

What is claimed is:

1. An alkali metal sulfonate mixture, the mixture consisting essentially of a reaction product of a first synthetic mono-hydrocarbyl substituted sulfonic acid having from about 20 to about 50 carbon atoms in the hydrocarbyl substituent, a second synthetic mono-hydrocarbyl substituted sulfonic acid having from about 10 to about 16 carbon atoms in the hydrocarbyl substituent, and an inorganic alkali metal base, wherein the reaction product has a number average molecular weight ranging from about 400 to about 425 and a substantially bimodal molecular weight distribution of a neutral mono-hydrocarbyl substituted sulfonate mixture, wherein the sulfonate mixture provides a substantially stable emulsion suitable for metal working applications in an aqueous emulsion of the sulfonate mixture and from about 80 to about 99 percent by weight water.

2. The alkali metal sulfonate mixture of claim 1, wherein the first synthetic monohydrocarbyl substituted sulfonic acid is selected from the group consisting of dimerized propylene tetramer benzene sulfonic acid and dimerized butylenes tetramer benzene sulfonic acid.

3. The alkali metal sulfonate mixture of claim 2, wherein the second synthetic monohydrocarbyl substituted sulfonic acid is selected from the group consisting of linear dodecylbenzene sulfonic acid and branched dodeceylbenzene sulfonic acid.

4. The alkali metal sulfonate mixture of claim 1, wherein the second synthetic monohydrocarbyl substituted sulfonic acid is selected from the group consisting of linear dodecylbenzene sulfonic acid and branched dodeceylbenzene sulfonic acid.

5. The alkali metal sulfonate mixture of claim 1, wherein the inorganic alkali metal base is selected from the group consisting of sodium hydroxide, potassium hydroxide, lithium hydroxide, sodium carbonate, potassium carbonate, and lithium carbonate.

6. The alkali metal sulfonate mixture of claim 1, wherein the first synthetic monohydrocarbyl substituted sulfonic acid has a number average molecular weight ranging from about 500 to about 900.

7. The alkali metal sulfonate mixture of claim 1, wherein the second synthetic monohydrocarbyl substituted sulfonic acid has a number average molecular weight ranging from about 300 to about 380.

8. The alkali metal sulfonate mixture of claim 1, wherein the mixture contains from about 50 to about 60 percent by weight active sulfonate.

9. A metalworking fluid composition comprising the alkali metal sulfonate mixture of claim 1.

10. The metalworking fluid composition of claim 9, further comprising a succinimide dispersant having a weight average molecular weight ranging from about 750 to about 1500 Daltons.

11. A method for working metals comprising applying a metalworking fluid composition comprising the alkali metal sulfonate mixture of claim 1 to the metal.

12. A concentrate for a metalworking fluid composition, the concentrate comprising from about 0.5 wt. % to about 85 wt. % of the alkali metal sulfonate mixture of claim 1.

13. A method for making an alkali metal sulfonate mixture having improved properties, the method comprising the steps of:
   charging a mixture of sulfonic acids to a reaction vessel, the mixture of sulfonic acids consisting essentially of a first synthetic mono-hydrocarbyl substituted sulfonic acid having from about 20 to about 50 carbon atoms in the hydrocarbyl substituent, and a second synthetic mono-hydrocarbyl substituted sulfonic acid having from about 10 to about 16 carbon atoms in the hydrocarbyl substituent;
   neutralizing the mixture of sulfonic acids with an alkali metal inorganic base selected from the group consisting of sodium hydroxide, potassium hydroxide, lithium hydroxide, sodium carbonate, potassium carbonate, and lithium carbonate to form a reaction product in an oleaginous reaction medium; and
   removing water from the reaction product to provide the alkali metal sulfonate mixture, wherein the mixture has a number average molecular weight ranging from about 400 to about 425 and a substantially bimodal molecular weight distribution of a neutral mono-hydrocarbyl substituted sulfonate mixture, and wherein the sulfonate mixture provides a substantially stable emulsion suitable for metal working applications in an aqueous emulsion of the sulfonate mixture and from about 80 to about 99 percent by weight water.

14. The method of claim 13, wherein the first synthetic mono-hydrocarbyl substituted sulfonic acid is selected from the group consisting of dimerized propylene tetramer benzene sulfonic acid and dimerized butylenes tetramer benzene sulfonic acid.

15. The method of claim 14, wherein the second synthetic mono-hydrocarbyl substituted sulfonic acid is selected from the group consisting of linear dodecylbenzene sulfonic acid and branched dodeceylbenzene sulfonic acid.

16. The method of claim 13, wherein the second synthetic mono-hydrocarbyl substituted sulfonic acid is selected from the group consisting of linear dodecylbenzene sulfonic acid and branched dodeceylbenzene sulfonic acid.

17. The method of claim 13, wherein the first synthetic mono-hydrocarbyl substituted sulfonic acid has a number average molecular weight ranging from about 500 to about 900.

18. The method of claim 13, wherein the second synthetic mono-hydrocarbyl substituted sulfonic acid has a number average molecular weight ranging from about 300 to about 380.

19. The method of claim 13, wherein the alkali metal sulfonate mixture contains from about 50 to about 60 percent by weight active sulfonate.

20. A method for working metals comprising applying a metalworking fluid composition comprising the alkali metal sulfonate mixture made by the method of claim 13 to the metal.

* * * * *

UNITED STATES PATENT AND TRADEMARK OFFICE
CERTIFICATE OF CORRECTION

PATENT NO.       : 7,601,676 B2                                              Page 1 of 1
APPLICATION NO. : 11/174312
DATED            : October 13, 2009
INVENTOR(S)      : Stoneman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 631 days.

Signed and Sealed this

Fifth Day of October, 2010

David J. Kappos
*Director of the United States Patent and Trademark Office*